(12) United States Patent
Fujii

(10) Patent No.: US 8,297,955 B2
(45) Date of Patent: Oct. 30, 2012

(54) ROLLER PUMP

(75) Inventor: Junya Fujii, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 908 days.

(21) Appl. No.: 12/161,721

(22) PCT Filed: Nov. 24, 2006

(86) PCT No.: PCT/JP2006/323393
§ 371 (c)(1),
(2), (4) Date: Jul. 22, 2008

(87) PCT Pub. No.: WO2007/086186
PCT Pub. Date: Aug. 2, 2007

(65) Prior Publication Data
US 2010/0224547 A1    Sep. 9, 2010

(30) Foreign Application Priority Data

Jan. 26, 2006  (JP) ................................. 2006-017904

(51) Int. Cl.
F04B 43/08    (2006.01)
F04B 43/12    (2006.01)
F04B 45/06    (2006.01)

(52) U.S. Cl. ................ 417/477.11; 417/477.9; 604/6.11

(58) Field of Classification Search ................. 417/476, 417/477.6, 477.9, 477.11, 477.1; 604/4.01, 604/6.11
See application file for complete search history.

(56) References Cited

U.S. PATENT DOCUMENTS

| 4,229,299 A * | 10/1980 | Savitz et al. ................... 210/85 |
| 4,256,442 A * | 3/1981 | Lamadrid et al. ........ 417/477.11 |
| 2003/0042862 A1 * | 3/2003 | O'Connor et al. ............ 318/560 |
| 2005/0254978 A1 * | 11/2005 | Huber et al. ............... 417/477.1 |

FOREIGN PATENT DOCUMENTS

| CN | 2199328 | 5/1995 |
| JP | 56-45616 | 10/1981 |
| JP | 56-45616 Y2 | 10/1981 |
| JP | 61-55184 U | 4/1986 |
| JP | 62-99250 | 6/1987 |
| JP | 63-141887 | 9/1988 |

(Continued)

OTHER PUBLICATIONS

English language Abstract of JP 2005-256817 A, Sep. 22, 2005.

(Continued)

Primary Examiner — Peter J Bertheaud
(74) Attorney, Agent, or Firm — Greenblum & Bernstein P.L.C.

(57) ABSTRACT

Provided is a roller pump that can easily install/remove an elastic tube and appropriately control a discharge flow rate. The roller pump includes a pump slide that is connected to a pump block cover via two slider links and restricts an arrangement of the elastic tube by an inner peripheral surface; a pump block cover that operates an opened state and a closed state of the pump slide; a first slider link that has a substantially circular contact surface in contact with the second slider link, having one end rotatably connected to the pump slide using a support pin and the other end rotatably connected to the pump block cover using a support pin; and a second slider link that has a substantially circular contact surface in contact with the first slider link and is rotatably connected to a fixed part of a base using a support pin.

10 Claims, 5 Drawing Sheets

FOREIGN PATENT DOCUMENTS

| | | |
|---|---|---|
| JP | 63-141887 U | 9/1988 |
| JP | 64-2767 Y2 | 1/1989 |
| JP | 6-142190 | 5/1994 |
| JP | 6-142190 A | 5/1994 |
| JP | 2005-256817 | 9/2005 |
| JP | 2005-256817 A | 9/2005 |

OTHER PUBLICATIONS

English language Abstract of JP 6-142190 A, May 25, 1994.
A partial English translation (Lines 8 to 19 in col. 6, Fig. 3) of JP 64-2767, Jan. 24, 1989.
A partial English translation (Lines 9 to 16 on pp. 2, Figs. 1, 2 and 10)of CN 2199328, May 31, 1995.

* cited by examiner (a) Full Opened State (b) Full Closed State (b) Full Closed State (a) Full Opened State

ROLLER PUMP

TECHNICAL FIELD

The present invention relates to a roller pump that delivers liquid such as blood, dialysis fluids, or medicines by pressingly closing an elastic tube using a roller rotating device. More particularly, the present invention relates to a roller pump suitable for medical applications.

BACKGROUND ART

Conventionally, for blood purification for, for example, renal function insufficiency patients, medical treatments by a continuous blood purification method such as Continuous Hemofiltration (CHF), Continuous Hemodia (CHD), and Continuous Hemodiafiltration (CHDF) have been performed.

A dialysis apparatus performing such a blood purification method or a blood artificial dialysis generally delivers liquid contained in an elastic tube by mounting a roller pump in a liquid circuit.

One example of such a roller pump has been disclosed, for example, in Patent Reference 1, having a conventional structure of sliding and spreading a pump housing thereby improving efficiency of installing/removing of a tube in/from the roller pump. In the roller pump disclosed in Patent Reference 1, an operation lever is reciprocated between an opened position and a closed position to drive a stator forwards/afterwards, arm parts are moved along guide holes to install/remove a tube.

Patent Reference 1: Japanese Unexamined Patent Application Publication No. 6-142190

DISCLOSURE OF INVENTION

Problems that Invention is to Solve

However, the above-described roller pump disclosed in Patent Reference 1 has a problem that, while improving the efficiency of tube installing/removing, the increase of the number of parts makes it difficult to strictly ensure an interval precision between the pump housing and a roller, which fails to control a discharging flow rate of a fluid at high accuracy.

Moreover, it is desired to simplify an operation for installing/removing an elastic tube that is set in the roller pump arranged in a liquid circuit.

Thus, the present invention overcomes the above problem. It is an object of the present invention to provide a roller pump in/from which an elastic tube can be easily installed and removed, and which surely prevents the elastic tube from being accidentally released from the roller pump when the elastic tube should be set in the roller pump. It is another object of the present invention to provide a roller pump that can control a discharging flow rate at high accuracy, by ensuring an interval precision between (i) a slide part restricting an arrangement of the elastic tube and (ii) a roller.

Means to Solve the Problems

In accordance with an aspect of the present invention for achieving the objects, there is provided a roller pump that delivers a fluid contained in an elastic tube by pressingly closing the elastic tube using a roller of a roller rotating device positioned on a base, the roller pump including: a slide part that is movable to a direction of the roller, and restricts an arrangement of the elastic tube; an operation part that operates (i) an opened state of the slide part where the elastic tube is installed in or removed from the roller pump, or (ii) a closed state of the slide part where the elastic tube is held in the roller pump; and an inhibit part that inhibits the slide part from moving to the opened state without the operation of the operation part, when the slide part is in the closed state.

With the above structure, the roller pump according to the present invention can ensure an appropriate interval precision between the slide part as a housing and the roller. As a result, the roller pump according to the present invention can control a discharging flow rate of the fluid at high accuracy.

The inhibit part may include a first link member and a second link member which are in contact with each other by respective substantially circular contact surfaces, the first link member has: one end rotatably connected to the slide part: and an other end rotatably connected to the second link member, and the second link member has: one end rotatably connected to the first link member: and an other end rotatably connected to a fixed part on the base, and a contact point between the first link member and the second link member exceeds a dead point of the second link member, when the slide part is changed from the opened state to the closed state.

With the above structure, while the slide part is in the closed state holding the elastic tube, a force of keeping the closed sate (hereinafter, referred to as "self-deterrence force") is applied in the roller pump, because the dead point has exceeded when the first link member and the second link member are changed from the opened state to the closed state. As a result, the roller pump according to the present invention can prevent that the elastic tube is accidentally released from the roller pump while the roller pump operates.

Effects of the Invention

In the roller pump according to the present invention, a slide part in slide-ably contact with an elastic tube slides to and from the elastic tube, so that the elastic tube can be easily set in the roller pump. Furthermore, the roller pump according to the present invention can ensure an appropriate interval precision between (i) the slide part restricting an arrangement of the elastic tube and (ii) a roller. Thereby, the roller pump according to the present invention can control a discharging flow rate at high accuracy, and can surely prevent the elastic tube from being accidentally released from the roller pump while the elastic tube should be set in the roller pump.

Figure 1:
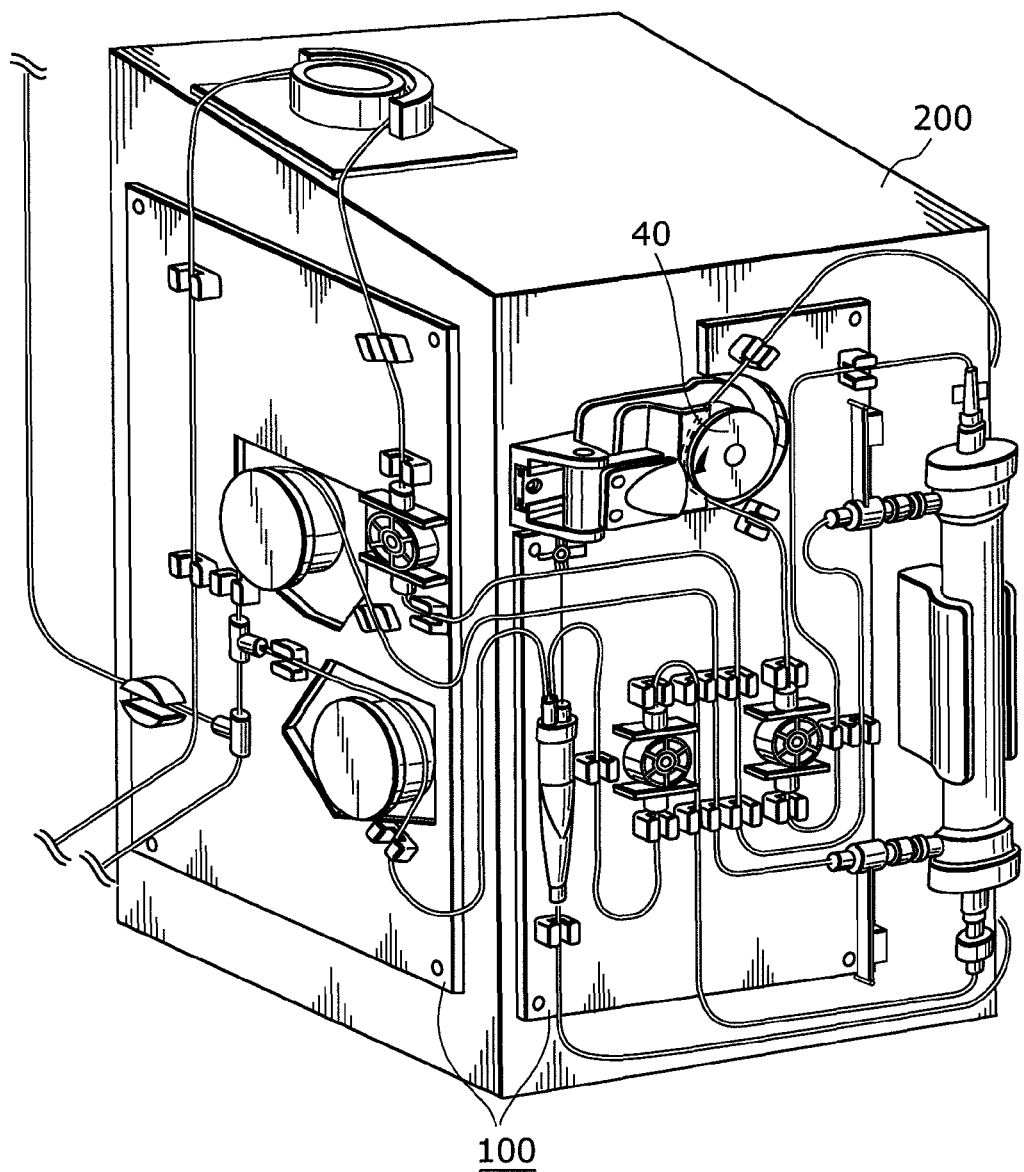
FIG. 1 is a perspective view of a dialysis apparatus using a roller pump according to an embodiment of the present invention.

NUMERICAL REFERENCES 1, 40 roller pump
2 roller head 3 roller
4, 44 pump slide
5, 41 pump block cover
6, 43 first slider link
7, 42 second slider link
8 support pin
9 pump block base
10, 45 base
11 motor
12 cover lock
13 tube guide
43a, 44a movement inhibit part
45a fixed part
100 liquid circuit body
200 dialysis apparatus body

BEST MODE FOR CARRYING OUT THE INVENTION

The following describes a roller pump according to the present invention with reference to the drawings.
(Embodiment)
FIG. 1 is a perspective view of a dialysis apparatus using a roller pump according to a preferred embodiment of the present invention.

As shown in FIG. 1, a dialysis apparatus that performs blood artificial dialysis includes: a liquid circuit body 100; and a dialysis apparatus body 200 having a driving unit that circulates liquid into the liquid circuit. In order to deliver the liquid, this dialysis apparatus uses, for example, a roller pump 40 that will be described later with reference to FIG. 4.

Figure 2:
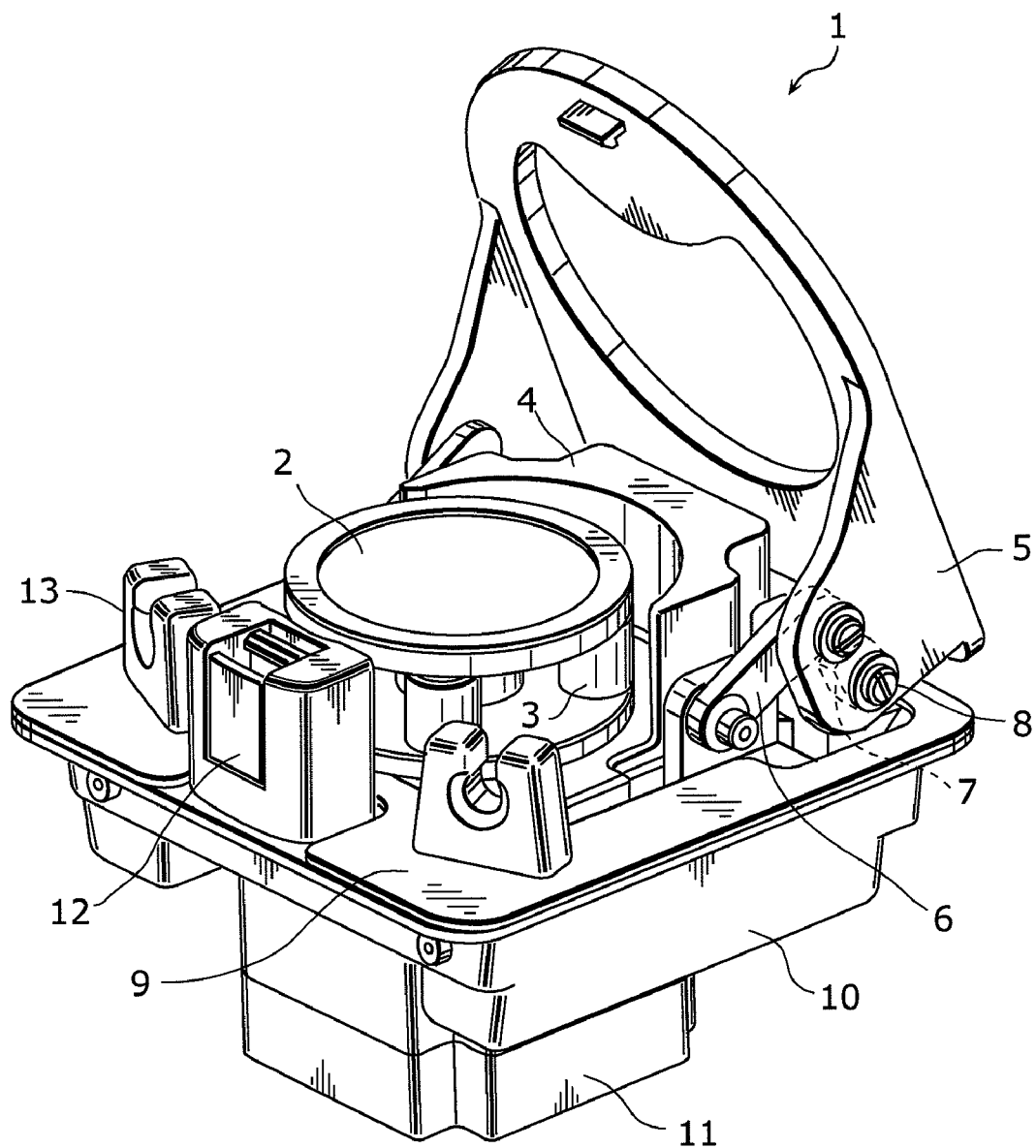
FIG. 2 is a perspective view of a roller pump according to the embodiment of the present invention.

FIG. 2 is a perspective view of a roller pump 1 according to an embodiment of the present invention.

The roller pump 1 according to the present embodiment is characterized in including a pump slide 4 that has a wall surface in slide-ably contact with an elastic tube and slides to and from the elastic tube, which makes it easy to install and remove the elastic tube in/from the roller pump 1. Furthermore, the roller pump 1 according to the present embodiment is characterized in having slider links 6 and 7 that inhibit undesired opening (an opened state) of the pump slide 4 when the elastic tube should be hold in the roller pump 1.

As shown in FIG. 2, the roller pump 1 includes a roller head 2, rollers 3, a pump slide 4, a pump block cover 5, a first slider link 6, a second slider link 7, a pump block base 9, a base 10, a motor 11, a cover lock 12, and tube guides 13. The roller head 2 is a roller rotating device that is connected to the motor 11 and delivers liquid contained in an elastic tube by rotating together with the rollers 3 by drive force of the motor 11. The rollers 3 are members arranged in the roller head 2. The rollers 3 deliver liquid contained in the elastic tube by pressing the elastic tube that is arranged along the pump slide 4. The pump slide 4 is connected with the pump block cover 5 via two slider links 6 and 7. The pump slide 4 restricts an arrangement of the elastic tube, when an inner peripheral surface of the pump slide 4 is in contact with the elastic tube. The pump block cover 5 operates an opened state and a closed state of the pump slide 4. The first slider link 6 has a substantially circular contact surface in contact with the second slider link 7. One end of the first slider link 6 is rotatably connected to the pump slide 4 using a support pin. The other end of the first slider link 6 is rotatably connected to the pump block cover 5 using a support pin. The second slider link 7 is rotatably connected to a fixed part formed on the base, using a support pin 8. The second slider link 7 has a substantially circular contact surface in contact with the first slider link 6. The pump block base 9 is integrally formed on the base of the roller pump 1. The pump block base 9 has the tube guides 13 that hold the elastic tube. The base 10 is included in the roller pump 1. The motor 11 is a driving unit that is connected to the roller head 2 and drives the roller head 2 to rotate. The cover lock 12 fastens the pump block cover 5 by being in connection to the pump block cover 5, when the elastic tube is set in the roller pump 1. The tube guide 13 holds the elastic tube at predetermined positions on the base.

According to the present embodiment, the pump slide 4 has a circular shape along a shape of circumference of the roller head 2. In addition, since the pump slide 4 is connected to the pump block cover 5 via the first slider link 6 and the second slider link 7, the pump slide 4 slides to and from the roller head 2 by opening and closing the pump block cover 5. As a result, an operator can install or remove the elastic tube by opening and closing the pump block cover 5.

Here, the elastic tube is to be set between an inner wall of the pump slide 4 and the roller 3. Then, rotating drive of the roller head 2 causes the rollers 3 to elastically press the elastic tube with a certain pressure, thereby pressingly feeding liquid contained in the elastic tube.

It should be noted that FIG. 2 shows three rollers 3 formed integrally in the roller head 2 at each 120-degree interval, but the rollers 3 may be two rollers arranged at a 180-degree interval, four rollers arranged at each 90-degree interval, or others.

It should also be note that the pump block cover 5 may have a shaft part that adjusts an interval between the roller head 2 and the pump slide 4, when the pump slide 4 is in a closed state where at least a part of the pump slide 4 contact the elastic tube, although this is not shown in FIG. 1. With the structure, positional adjustment of the shaft part enables the roller pump according to the present invention to be used for various elastic tubes having different radius. Moreover, a position of the pump slide 4 or a distance of sliding of the pump slide 4 can be changed depending of radius of the elastic tube. Here, the pump slide 4 of the roller pump 1 according to the present invention is an independent member, and connected to the base 10 using a spring member so that the pump slide 4 can be adjusted forwards and backwards depending on a size of the elastic tube.

As shown in FIG. 2, an angle of a contact surface between the pump slide 4 and the elastic tube is 120 degrees. Since use of two rollers causes roller slip regions which fails to press the tube, an angle of a contact surface of the rollers is generally 180 degrees. However, if a tube is installed or removed by moving the pump slide 4 in the manner as described above, a clearance between (i) an end of a part where the pump slide 4 is in contact with the tube and (ii) the tube is decreased. Thereby, 180 degrees of the contact surface is difficult to be achieved. Here, if the angle of the contact surface is decreased, it is necessary to increase the number of rollers to prevent that the roller is rotating but loses a contact with the elastic tube (namely, slipping). From the above reasons, a contact angle (δ) between the tube and the wall surface of the pump slide 4 is preferably from 100 degrees to 160 degrees. Therefore, it is desirable to form three or more rollers at equally-spaced intervals (angles).

Figure 3:
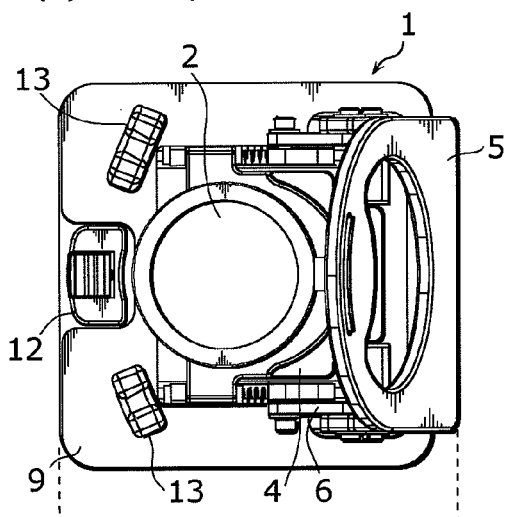
FIG. 3 shows a top view and a side view of the roller pump of FIG. 2 when a pump block cover is fully opened (in a full opened state) and when a pump block cover is fully closed (in a full closed state).
Figure 3:
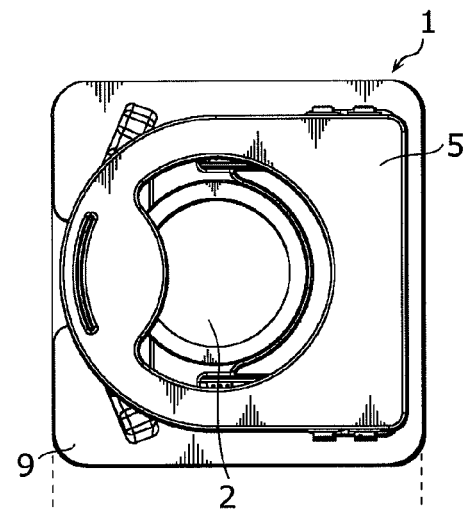
Figure 3:
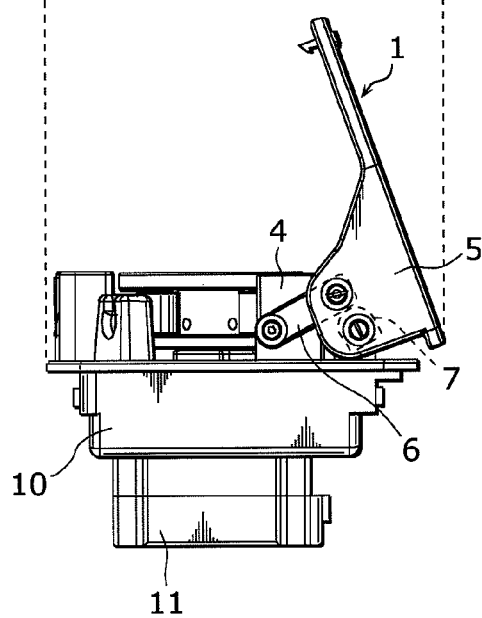
Figure 3:
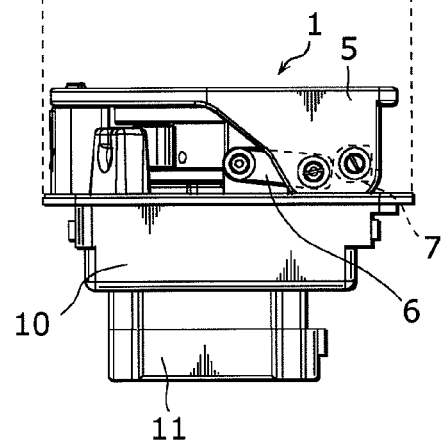

FIG. 3 shows a top view and a side view of the roller pump 1 of FIG. 2, when the pump block cover 5 is fully opened (in a full opened state) and when the pump block cover 5 is fully closed (in a full closed state).

In the full opened state as shown in FIG. 3(a), an elastic tube can be installed in or removed from the roller pump 1. Here, an operator can install or remove the elastic tube by a simple operation of opening and closing the pump block cover 5.

In the full closed state as shown in FIG. 3(b), the elastic tube is set and held in the roller pump 1. According to the present invention, locking of the first slider link 6 and the second slider link 7 produces the self-deterrence force for inhibiting a backward movement of the pump slide 4. Thereby, it is possible to surely prevent that the pump block cover 5, which is originally used to install or remove the elastic tube, is accidentally opened during use of the roller pump and eventually release the elastic tube.

In the full opened state of FIG. 3(a), an angle between the pump block cover 5 and the pump block base 9 is 70 degrees, and an angle between the first slider link 6 and the second slider link 7 is 90 degrees, for example. In the full closed state of FIG. 3(b), an angle between the first slider link 6 and the second slider link 7 is, for example, in a rage from −1 degree to −30 degrees, exceeding 0 degree. Preferably, the range is from −5 degrees to −20 degrees.

Figure 4:
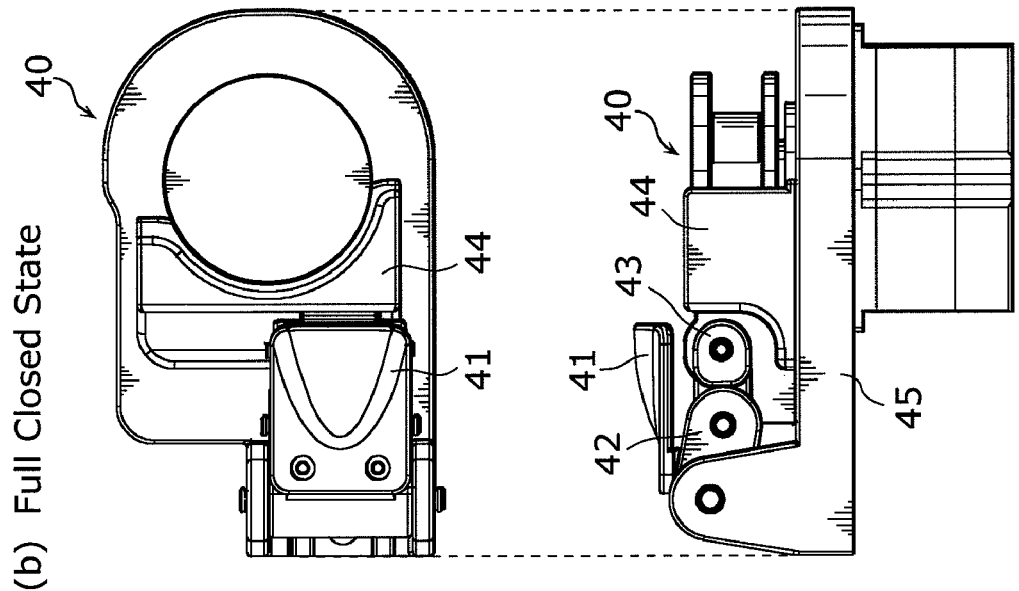
FIG. 4 shows a top view and a side view of a roller pump having a pump block cover different from the pump block cover of FIG. 2, when the pump block cover is fully opened (n a full opened state) and when the pump block cover is fully closed (in a full closed state).
Figure 4:
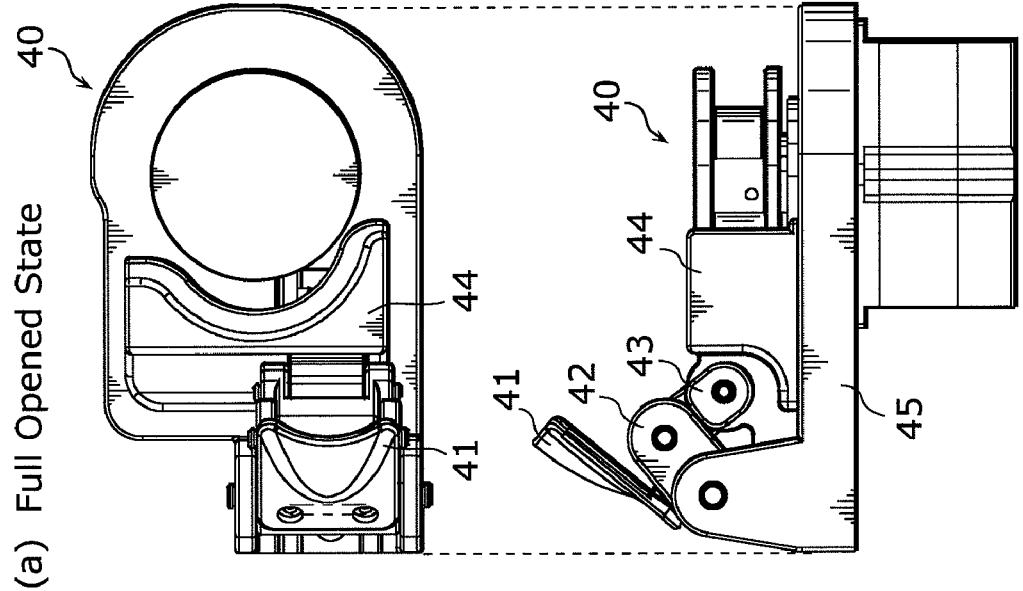

FIG. 4 shows a top view and a side view of the roller pump 40 having a pump block cover 41, in each of a full opened state and a full closed state. The pump block cover 41 in the roller pump 40 is different from the pump block cover 5 of the roller pump 1 of FIG. 2.

The roller pump 40 shown in FIG. 4 has the pump block cover 41 that is smaller than the pump block cover 5 of FIG. 2.

In the full opened state of FIG. 4(a), an elastic tube can be installed in or removed from the roller pump 40. Here, an operator can install or remove the elastic tube by a simple operation of opening and closing the pump block cover 41.

In the full opened state in FIG. 4(b), the elastic tube is set and held in the roller pump 40. According to the present invention, locking of a first slider link 43 and a second slider link 42 produces self-deterrence force for inhibiting a backward movement of a pump slide 44. Thereby, it is possible to surely prevent that the pump block cover 41, which is originally used to install or remove the elastic tube, is accidentally opened during use of the roller pump 40 and eventually release the elastic tube. Here, in the full closed state, an angle between the first slider link 43 and the second slider link 42 is, for example, in a rage from −1 degree to −30 degrees, exceeding 0 degree. Preferably, the range is from −5 degrees to −20 degrees.

Figure 5:
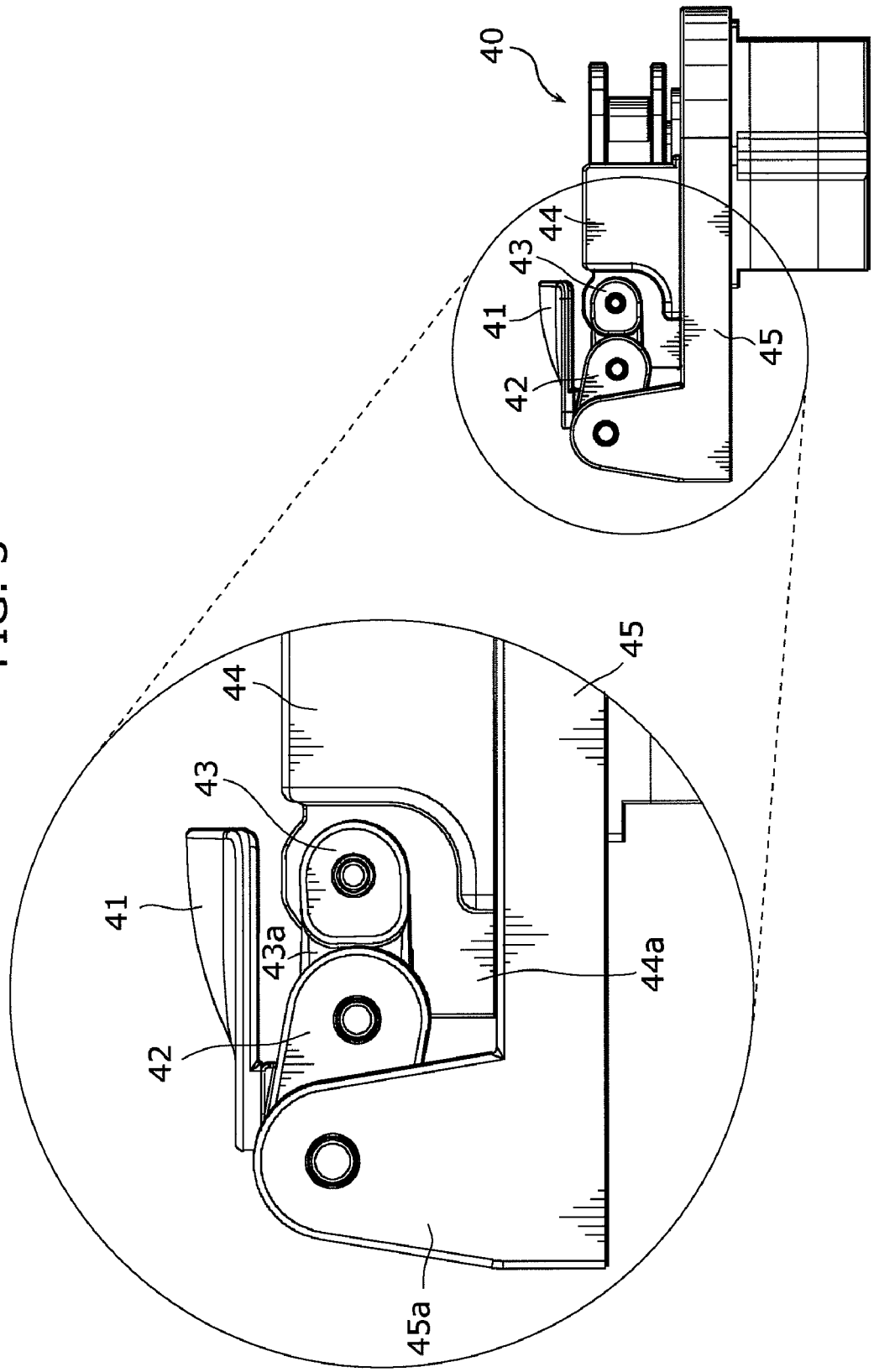
FIG. 5 is an enlarged side view of a part of slider links of the roller pump of FIG. 4(*b*).

FIG. 5 is an enlarged side view of a part of the slider links 42 and 43 of the roller pump 40 of FIG. 4(b).

As shown in FIG. 5, the pump slide 44 has a movement inhibit part 44a that inhibits a downward movement of the first slider link 43 and the second slider link 42.

The first slider link 43 has a movement inhibit part 43a at a position corresponding to the movement inhibit part 44, in order to inhibit a downward movement of the first slider link 43 and the second slider link 42.

When the first slider link 43 and the second slider link 42 are changed from the opened state to the closed state, if an angle between the first slider link 43 and the second slider link 42 exceeds a dead point even if a pressure is applied to the first slider link 43 and the second slider link 42 from an opposite side, the movement inhibit part 44a and the movement inhibit part 43a are in contact with each other to lock the first slider link 43 and the second slider link 42. This produces self-deterrence force for inhibiting an accidental backward movement of the pump slide 44. As a result, it is possible to surely prevent that the pump block cover 41, which is originally used to install or remove an elastic tube, is accidentally opened during use of the roller pump and eventually release the elastic tube. Thereby, it is possible to surely prevent the pump slide 44 from moving backwards without operating the pump block cover 41 in the closed state.

Moreover, at the edge of a base 45 of the roller pump 40, a fixing part 45a is formed. One end of the second slider link 42 is rotatably connected to the fixing part 45a using a support pin. Closing of the fixing part 45a restricts a backward movement of the second slider link 42 when the pump block cover 41 is in the closed state.

With the above structure shown in FIG. 5, it is possible to prevent a backward movement of the pump slide 44 and accidental release of an elastic tube when the elastic tube is set in the roller pump 40.

As described above, in the roller pump 1 according to the present embodiment, the pump slide 4 slides to and from the elastic tube by operating the pump block cover 5. As a result, the roller pump 1 according to the present embodiment can install and remove the elastic tube in/from the roller pump 1 more easily.

Furthermore, in the roller pump according to the present embodiment, when the pump block cover 5 is in the closes state, the pump slide 4 can not move backwards. Thereby, this prevents the pump slide 4 from accidentally moving backwards, thereby surely preventing the elastic tube from releasing from the roller pump when the elastic tube is set in the roller pump. In addition, this can keep a proper interval precision between the inner peripheral surface of the pump slide 4 and the roller 3. As a result, it is possible to keep high accuracy of a discharging flow rate of a fluid in the elastic tube, and achieve more stable delivering by an dialysis apparatus or the like using the roller pump 1 of the present invention.

Although only some exemplary embodiments of the roller pump of the present invention have been described in detail above, those skilled in the art will be readily appreciate that many modifications are possible in the exemplary embodiments without materially departing from the novel teachings and advantages of the present invention. Accordingly, all such modifications are intended to be included within the scope of this invention.

INDUSTRIAL APPLICABILITY

The roller pump according to the present invention can be used as a roller pump used in an apparatus for circulating and supplying liquid such as blood or dialysis fluids by an elastic tube in the field of medical treatments. For example, the roller pump according to the present invention can be used as a roller pump that performs liquid delivering in artificial dialysis apparatuses and the like.

The invention claimed is:

1. A roller pump that delivers a fluid contained in an elastic tube by pressingly closing the elastic tube using a roller of a roller rotating device positioned on a base, said roller pump comprising:
 a slide part that is movable in a direction toward the roller, and restricts an arrangement of the elastic tube;
 an operation part that operates said slide part to move backward to an opened state, where the elastic tube is installed in or removed from said roller pump, or forward to a closed state, where the elastic tube is held in said roller pump; and
 an inhibit part that inhibits said slide part from moving from the closed state to the opened state without the operation of said operation part,
 wherein said inhibit part includes a first link member and a second link member which are in contact with each other by respective curved contact surfaces,
 said first link member has a first end rotatably connected to said slide part and a second end arranged to rotate against a first end of said second link member, said first end of said second link member being rotatably coupled to said second end of said first link member through engagement between said respective curved contact surfaces such that said second end of said first link member and said first end of said second link member rotatably contact each other along said respective curved contact surfaces, and a second end of said second link member is rotatably coupled to a fixed part on the base, and wherein when said slide part is moved to the closed state, a contact point between said first link member and said second link member, along said respective curved contact surfaces, locks said first link member and said second link member, thereby inhibiting backward movement of said slide part.

2. The roller pump according to claim 1, wherein the operation of said operation part induces rotation of said first link member and said second link member.

3. The roller pump according to claim 1, wherein said operation part changes said slide part from the closed state to the opened state by rotating and shifting a portion which connects said first link member to said second link member.

4. The roller pump according to claim 1, wherein the roller rotating device includes at least three rollers, and wherein at least one of the at least three rollers is arranged to achieve a predetermined angle.

5. The roller pump according to claim 1, further comprising an interval change unit that changes an interval between an inner peripheral surface of said slide part and the roller in the closed state.

6. A blood dialysis apparatus comprising the roller pump according to claim 1.

7. A blood dialysis apparatus comprising the roller pump according to claim 2.

8. A blood dialysis apparatus comprising the roller pump according to claim 3.

9. A blood dialysis apparatus comprising the roller pump according to claim 4.

10. A blood dialysis apparatus comprising the roller pump according to claim 5.

* * * * *